US00PP30312P2

(12) United States Plant Patent
Hoogendoorn

(10) Patent No.: US PP30,312 P2
(45) Date of Patent: Mar. 26, 2019

(54) ***MILTONIDIUM* ORCHID PLANT NAMED 'CAMBLOQA'**

(50) Latin Name: ***Nothogenus:* x *Miltonidium***
Varietal Denomination: CAMBLOQA

(71) Applicant: Anthura B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,431

(22) Filed: Nov. 10, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O. Robinson
(74) *Attorney, Agent, or Firm* — Jondle & Associates, P.C.

(57) ABSTRACT

A new and distinct variety of x *Miltonidium* plant named 'CAMBLOQA', particularly characterized by having dark red flowers with a large dark red-purple lip, 1-4 peduncles that are medium long and sturdy, leaves that are lanceolate and elongated to very elongated, and is propagated by meristem tissue culture is disclosed.

3 Drawing Sheets

Genus and species:
Nothogenus: x *Miltonidium.*
Variety denomination: 'CAMBLOQA'.

BACKGROUND OF THE NEW PLANT

The present invention comprises a new and distinct cultivar of x *Miltonidium* plant, botanically known as x *Miltonidium* of the Orchidaceae family, and hereinafter referred to by the cultivar name 'CAMBLOQA'.

*Miltonia, Oncidium* and *Brassia* and some other genera are a complex group of orchid species that are easily hybridized. The boundaries between the genera have been under discussion for the last several decades. According to the most recent classification by Pridgeon, Cribb, Chase and Rasmussen (Genera Orchidacearum), the plant herein described is most likely a complex hybrid between *Miltonia* and *Oncidium* species, hence called x *Miltonidium.*

All x *Miltonidium* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth), with two leaves on each side. The peduncles vary in size from 20-70 cm.

x *Miltonidium* orchids are used as flowering potted-plants for home or interiorscape. x *Miltonidium* produces upright or pendent lateral racemes or panicles, often with many showy flowers which open in succession beginning with the lowermost. The flowers possess three sepals and two petals, the lateral ones being alike and having a peculiar labellum. Flower colors include various shades of pink, white, yellow, and red-brown.

x *Miltonidium* orchids are typically propagated from tissue culture. Asexual propagation of x *Miltonidium* is often done from off-shoots which arise from the lower bracts of the inflorescence. The resulting plants are detached from the mother plants and may be planted in a suitable substrate.

The new x *Miltonidium* 'CAMBLOQA' is particularly characterized by its attractive and unique dark red flowers with a large dark red-purple lip, economical propagation by tissue culture, early flowering, and a plant dimension suitable for packaging and shipping to the market.

'CAMBLOQA' is a product of a planned breeding program conducted by the inventor in Bleiswijk, The Netherlands.

The new x *Miltonidium* 'CAMBLOQA' originated from a cross made by the inventor in January 2005 in Bleiswijk, The Netherlands. The female parent is an orange x *Miltonidium* pot plant named '60000-0149' (unpatented) and the male parent is a greyed-purple *Oncidium* pot plant named '60000-0165' (unpatented). A single plant was selected by the inventor from within the progeny of the stated cross-pollination in a controlled greenhouse in Bleiswijk, The Netherlands in July 2008.

Asexual reproduction of 'CAMBLOQA' by meristem tissue culture since 2011 in Bleiswijk, The Netherlands has demonstrated that the new variety reproduces true to type with all of the characteristics, as herein described, firmly fixed and retained through successive generations.

Plant Breeder's Rights for this variety have been applied for in Europe on Nov. 25, 2016. 'CAMBLOQA' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands.

1) Dark red flower with a large dark red-purple lip;
2) 1-4 peduncles;
3) Peduncle is medium long and sturdy;

4) The shape of the leaf is lanceolate and elongated to very elongated; and
5) Plants are propagated by meristem tissue culture.

DESCRIPTION OF THE PHOTOGRAPHS

This new x *Miltonidium* plant is illustrated by the accompanying photographs which show the overall plant habit including blooms, buds and foliage of the plant; the colors shown are as true as can be reasonably obtained by conventional photographic procedures. The photographs are of a 70-week old plant grown in a greenhouse in Bleiswijk, The Netherlands in September 2017.

DESCRIPTION OF THE NEW VARIETY

Figure 1:
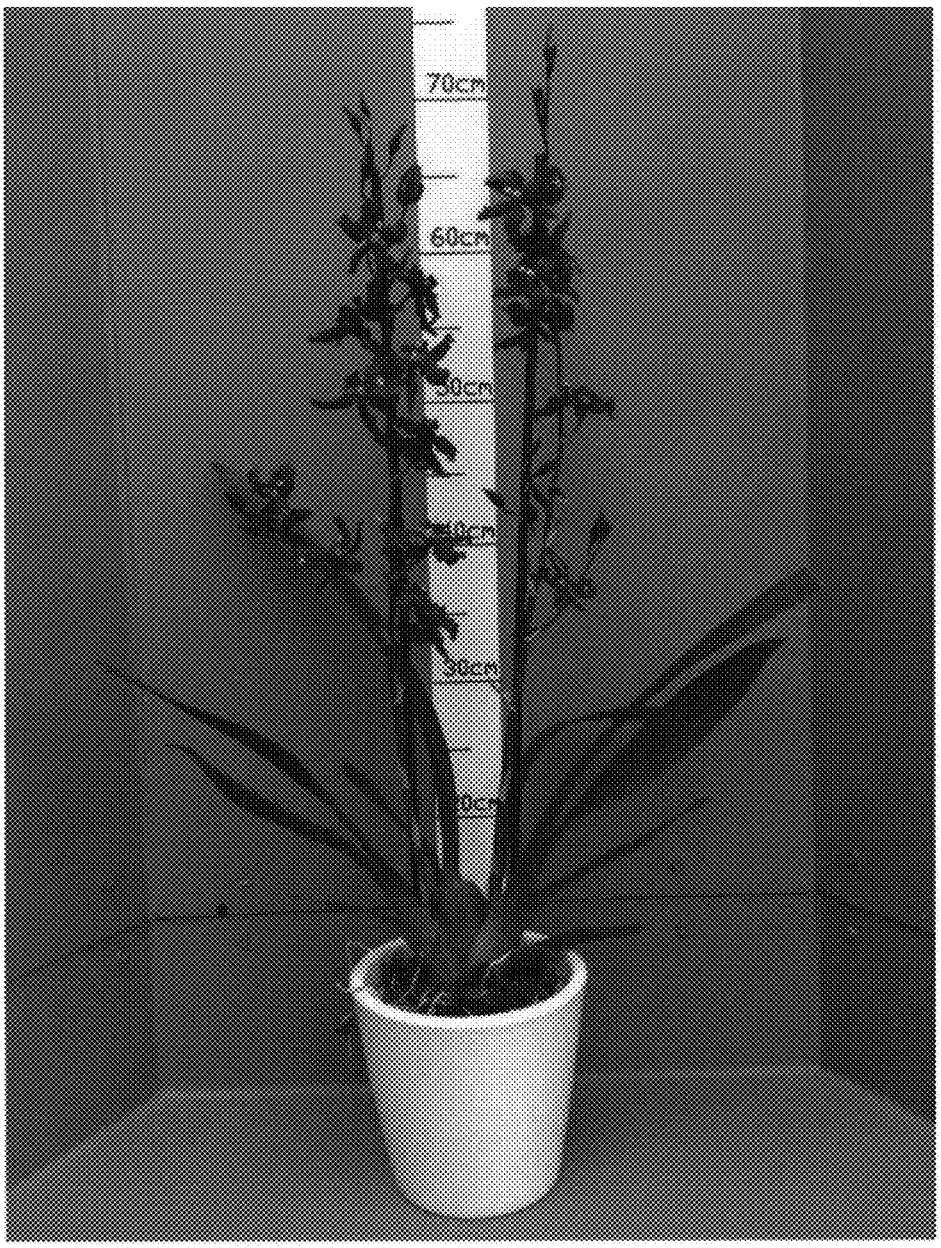
FIG. 1 shows the overall plant habit, including blooms, buds and foliage of 'CAMBLOQA'.
Figure 2:
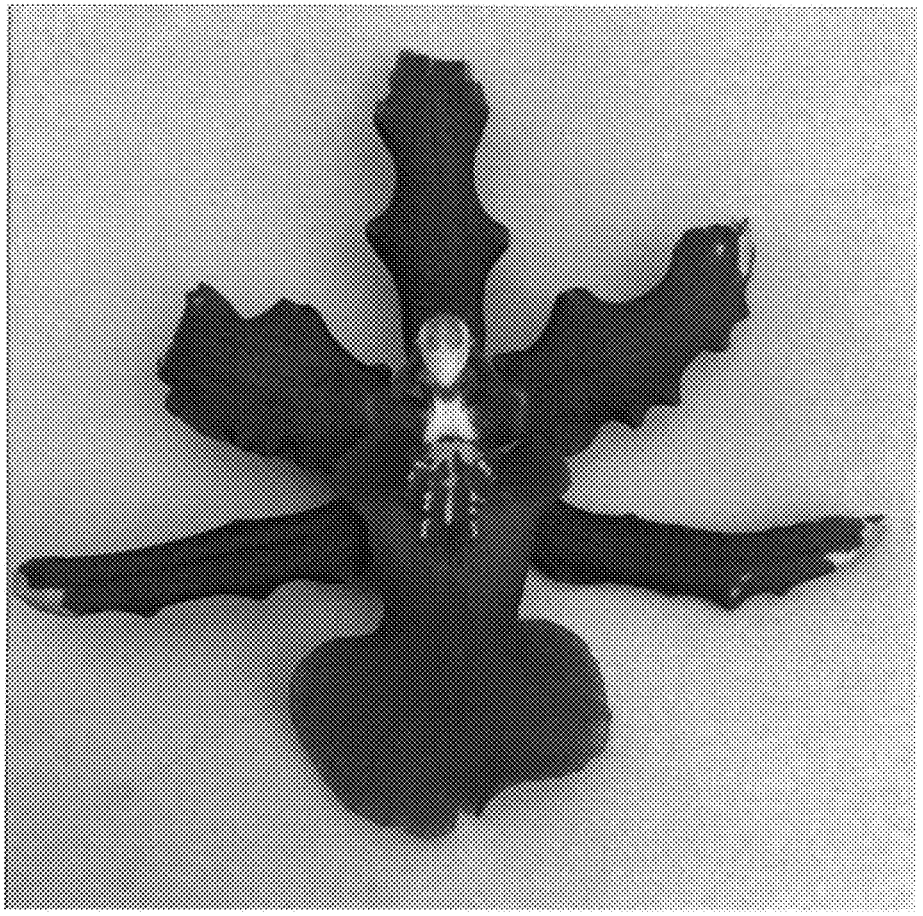
FIG. 2 shows a close-up of a flower of 'CAMBLOQA'.
Figure 3:
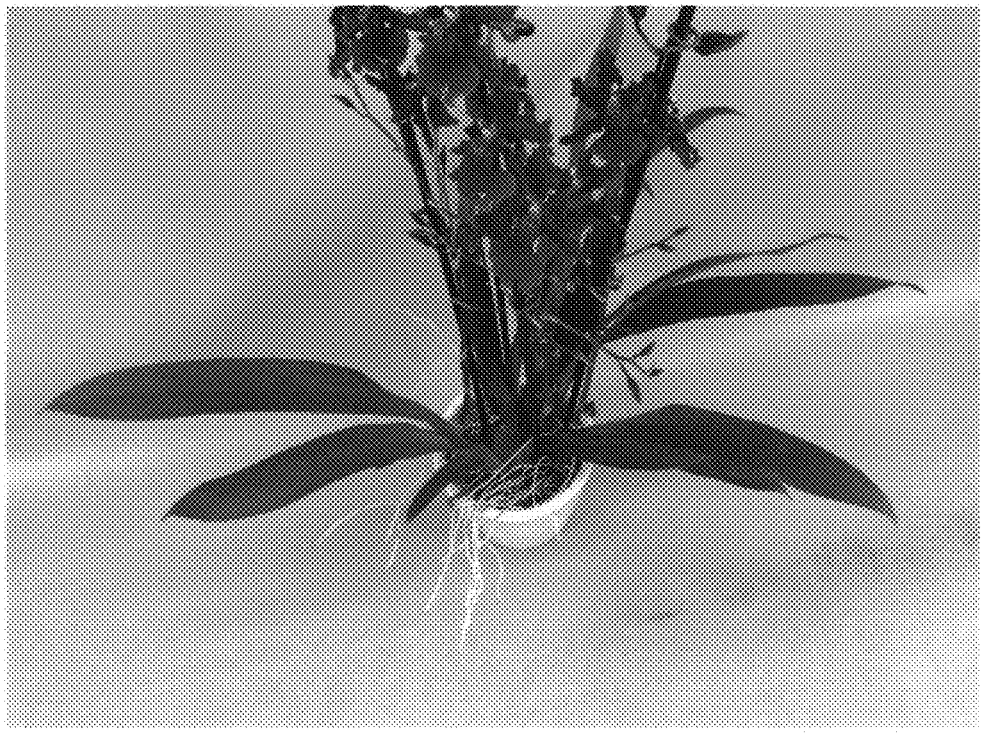
FIG. 3 shows a top view of the leaves of 'CAMBLOQA'.

The following detailed description sets forth the distinctive characteristics of 'CAMBLOQA'. The data which define these characteristics were collected from asexual reproductions carried out in Bleiswijk, The Netherlands. The plant history was taken on 70-week old plants which were planted from tissue culture to a plug and then to 12 centimeter pots, and grown in a greenhouse between 20° C. to 25° C. Observations were made in September 2017. Color readings were taken under 4000-6000 lux natural light in the greenhouse. Color references are primarily to The R.H.S. Colour Chart of The Royal Horticultural Society of London (R.H.S.) (2015).

DETAILED BOTANICAL DESCRIPTION

Classification:
- *Family*.—Orchidaceae.
- *Botanical*.—x *Miltonidium*.
- *Common name*.—Cambria.
- *Variety name*.—'CAMBLOQA'.

Parentage:
- *Female parent*.—x *Moltonidium* cultivar '60000-0149' (unpatented).
- *Male parent*.—*Oncidium* cultivar '60000-0165' (unpatented).

Propagation:
- *Type*.—Meristem tissue culture.

Plant:
- *Crop time* (*time to produce a finished flowering plant*).—50 to 70 weeks for a 12 cm pot.
- *Growth habit of peduncle*.—Standard, green leaves, raceme to panicle.
- *Height* (*including pot, including inflorescence*).—65.0 cm to 75.0 cm.
- *Width* (*measured from leaf tips*).—45.0 cm to 50.0 cm.
- *Vigor*.—Strong.

Roots:
- *Root description*.—Greyed-yellow (RHS 161D) colored roots lightly branching with light green growing tips (RHS 145D) (The exact shades of yellow and green may vary with minimal changes of environmental conditions).

Pseudobulb:
- *Number of pseudobulbs*.—1.
- *Shape*.—Laterally compressed ovoid.
- *Length*.—6.0 cm to 6.5 cm.
- *Width*.—4.0 cm to 4.5 cm.
- *Thickness*.—1.5 cm to 2.0 cm.
- *Color*.—Green (RHS 146A).

Leaves:
- *Mature leaves*.—Quantity per pseudobulb: 12 to 14 leaves are produced before flowering. Length (fully expanded): 35.0 cm to 40.0 cm. Width: 4.5 cm to 5.5 cm. Attitude of the leaves: Erect. Shape: Lanceolate. Base shape: Elongated to very elongated. Apex: Acute. Leaf margin: Entire. Color: Upper surface: RHS 147A. Lower surface: RHS 147B. Texture: Upper surface: Slightly rough. Lower surface: Smooth. Thickness: 0.6 mm to 0.8 mm. Venation: Pattern: Parallel. Color of the midvein: Upper surface: RHS 147A. Lower surface: RHS 147B.

Peduncle:
- *Quantity per plant*.—1 to 4.
- *Number of flowers per peduncle*.—11 to 18.
- *Length*.—From 54.0 cm to 64.0 cm.
- *Diameter*.—5.0 mm to 6.0 mm.
- *Thickness*.—Medium.
- *Strength*.—Strong.
- *Aspect*.—Upright.
- *Texture*.—Smooth.
- *Color*.—Green (RHS 146A).
- *Internode length*.—35.0 mm to 45.0 mm.
- *Number of branches*.—0 to 4.
- *Callosities*.—None.

Inflorescence description:
- *Appearance*.—Upright, panicle inflorescence with bilaterally symmetrical flowers that open in succession beginning with the lowermost flower.
- *Inflorescence size*.—Height (from base to tip): 200.0 mm to 240.0 mm.
- *Flowering time*.—First flowers can be expected 4 to 6 months after planting in a 12 cm pot.
- *Number of flowers in the inflorescence*.—15 to 30.
- *Flower*.—Height: 60.0 mm to 65.0 mm. Diameter: 55.0 mm to 60.0 mm.
- *Flower longevity*.—On the plant: 5 to 8 weeks.
- *Fragrance*.—Present; a light, sweet, complex fragrance. Degree of the fragrance: Weak.
- *Petals*.—Shape: Elliptic. Apex: Acute. Margin: Undulated. Curvature: Recurving. Curvature of the longitudinal axis: Moderately recurving. Length (from base to tip): 30.0 mm to 32.0 mm. Width: 13.0 mm to 15.0 mm. Color (when fully opened): Upper surface: Basic color: Dark red (RHS 187A). Over color: Light green tips (RHS 195D). Lower surface: Basic color: Dark red (RHS 187A). Over color: Light green (RHS 195C) in the middle.
- *Dorsal sepal*.—Shape: Elliptic. Apex: Acute. Margin: Undulated. Curvature: Incurving. Curvature of the longitudinal axis: Moderately incurving. Length (from base to tip): 31.0 mm to 33.0 mm. Width: 13.0 mm to 15.0 mm. Color (when fully opened): Upper surface: Basic color: Dark red (RHS 187A). Over color: Light green (RHS 195C). Lower surface: Basic color: Dark red (RHS 187A). Over color: Light greyed-green (RHS 195B) in the middle.
- *Lateral sepals*.—Shape: Elliptic. Margin: Undulated. Curvature: Recurving. Curvature of the longitudinal axis: Moderately recurving. Length (from base to tip): 34.0 mm to 36.0 mm. Width: 12.0 mm to 14.0 mm. Color (when fully opened): Upper surface:

Basic color: Dark red (RHS 187A). Over color: Small light green tips (RHS 195C). Lower surface: Basic color: Light greyed-green (RHS 195B). Over color: Dark red edges (RHS 187A).

*Labellum* (*lip*).—Length: 31.0 mm to 33.0 mm. Width: 29.0 mm to 31.0 mm.

*Lateral lobe*.—Size in relation to apical lobe: Smaller. Color: Upper surface: Dark red (RHS 187A). Lower surface: Dark red (RHS 187B).

*Apical lobe*.—Margin: Undulated. Color: Upper surface: Dark red-purple (RHS 187A and N79C) with white region (RHS NN155C) toward the edge. Lower surface: Dark red-purple (RHS 187C and N77B) with light green (RHS 195C) over color.

*Callus*.—Color: Dark red (RHS 187A) with yellow tips (RHS 12B). Shape: Indescribable. Average size: Indescribable. Average number of protuberance: 3 to 5.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 10.0 mm to 12.0 mm. Diameter: 4.5 mm to 4.8 mm. Color: Dark red (RHS 187A). Wings: Absent.

*Cap*.—Average size: 1.0 mm to 3.0 mm. Shape: Oval cup shape. Color: White (RHS 155C) with red-purple top (RHS N77B).

*Pollinia*.—Quantity: 2. Diameter: 0.8 mm to 1.0 mm. Color: Yellow (RHS 13A).

*Ovary*.—Length: 6.0 mm to 8.0 mm. Diameter: 2.2 mm to 2.4 mm.

*Pedicel*.—Length: 25.0 mm to 27.0 mm. Diameter: 2.3 mm to 2.6 mm. Color: Green (RHS 144B) at the base; dark red (RHS 187A) toward the flower.

Disease, pest, and stress resistance: No specific resistance or susceptibility observed to date.

Temperature tolerance: Not observed to date.

COMPARISON WITH PARENTAL AND SIMILAR VARIETIES

The female parent plant of 'CAMBLOQA', cultivar '60000-0149' (unpatented), is no longer in existence, so a meaningful comparison cannot be made.

'CAMBLOQA' differs from male parent '60000-165' (unpatented) in that 'CAMBLOQA' has dark red flowers with light green tips and a dark red-purple lip with a white region toward the edge, whereas '60000-165' has light red-purple flowers and a purple-red lip with light purple toward the margin.

'CAMBLOQA' is most similar to the commercial x *Burrageara* plant named 'CAMBOPAL' (unpatented) and a x *Miltonidium* plant named 'CAMBOLYK' (U.S. Plant Pat. No. 28,026). 'CAMBLOQA' differs from commercial variety 'CAMBOPAL' in that 'CAMBLOQA' has dark red flowers with light green tips and a dark red-purple lip with a white region toward the edge, whereas 'CAMBOPAL' has brown-purple flowers and a purple lip with white irregular spots and dark red toward the callus. Additionally, 'CAMBLOQA' is a taller plant with larger flowers than 'CAMBOPAL'.

'CAMBLOQA' differs from commercial variety 'CAMBOLYK' in that 'CAMBLOQA' has dark red flowers with light green tips and a dark red-purple lip with a white region toward the edge, whereas 'CAMBOLYK' has dark red flowers and a red-purple lip with white irregular spots and darker red toward the callus. Additionally, 'CAMBLOQA' is a taller plant with larger flowers than 'CAMBOLYK'.

I claim:

1. A new and distinct variety of x *Miltonidium* plant named 'CAMBLOQA', substantially as described and illustrated herein.

* * * * *